(12) United States Patent
Andersson

(10) Patent No.: US 6,610,208 B1
(45) Date of Patent: Aug. 26, 2003

(54) DEVICE FOR REDUCING LOSS OF LIQUID DURING FRACTION COLLECTION

(75) Inventor: Lars Andersson, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 10/018,025

(22) PCT Filed: May 12, 2000

(86) PCT No.: PCT/SE00/00959

§ 371 (c)(1),
(2), (4) Date: Apr. 29, 2002

(87) PCT Pub. No.: WO00/70337

PCT Pub. Date: Nov. 23, 2000

(30) Foreign Application Priority Data

May 12, 1999  (SE) .............................................. 9901722

(51) Int. Cl.⁷ .............................................. B01D 15/08
(52) U.S. Cl. .................... 210/656; 210/659; 210/198.2; 73/61.56
(58) Field of Search ................................ 210/656, 659, 210/143, 198.2; 95/82; 96/102; 73/61.56; 422/70; 436/161

(56) References Cited

U.S. PATENT DOCUMENTS 4,077,444 A * 3/1978 Gilson ........................ 141/130
6,309,541 B1 * 10/2001 Maiefski ................... 210/198.2
6,355,164 B1 * 3/2002 Wendell ................... 210/198.2
6,413,428 B1 * 7/2002 Berger ...................... 210/198.2

FOREIGN PATENT DOCUMENTS

| DE | 4303275 | * | 8/1994 | ............. 210/198.2 |
| JP | 5926058 | * | 2/1984 | ............. 210/198.2 |
| JP | 6468657 | * | 3/1989 | ............. 210/198.2 |
| JP | 4134262 | * | 5/1992 | ............. 210/198.2 |

OTHER PUBLICATIONS

Dialog Web Abstract of DE 4303275 # 009982279.*
Dialog Web Abstract of Japan 10 68657 # 007855470.*
Dialog Web Abstract of Japan 4 134262 # 009077117.*
Dialog Web Abstract of Japan 59 026058 # 003926246.*

* cited by examiner

Primary Examiner—Ernest G. Therkorn
(74) Attorney, Agent, or Firm—Royal N. Ronning, Jr.; Stephen G. Ryan

(57) ABSTRACT

Spillage of liquid during switching of receptacles in a fraction collector is avoided by introducing a device in the flow path between an inlet tube and a dispensing means. The device includes an expandable chamber that accommodates liquid during the time interval for switching from one receptacle to the next receptacle.

6 Claims, 5 Drawing Sheets

DEVICE FOR REDUCING LOSS OF LIQUID DURING FRACTION COLLECTION

This application is a 371 of PCT/SE00/00959 filed May 12, 2000.

TECHNICAL FIELD OF THE INVENTION

The present invention relates to a device for use with fraction collectors, and more specifically to a device for preventing spillage when switching from one collecting receptacle to the next.

TECHNICAL BACKGROUND

Fraction collectors are widely used in many applications, such as in the field of liquid chromatography. A fraction collector is used for dispensing a flow of a liquid to a number of receptacles. The receptacles are typically constituted as test tubes mounted in a rack or as recesses formed in a plate. Two main working principles can be distinguished for fraction collectors: the rotatable collector wherein the receptacles are fed towards a dispensing means by a rotating movement, and the X-Y collector wherein the receptacles are fed towards a dispensing means by linear movements in one or two directions. Of course, these principles are the same as those for fraction collectors wherein the dispensing means is moving while the receptacles are at rest.

Regardless of the type of receptacle or fraction collector working principle, there is always a distance between each separate receptacle. Therefore, when switching from one receptacle to the next, a spillage of the dispensed liquid is likely to occur, especially in a case were the liquid flow is essentially continuous. There are numerous reasons for why such spillage is not desired: it could contain valuable substances, it could be a potential health hazard and the working area becomes messy.

Methods for avoiding the spillage are known. For example, in U.S. Pat. No. 4,077,444 to Gilson et al. there is described a valve and a valve operator that are used to discontinue a liquid flow through a dispensing tube in order to prevent spillage from the tube as it moves between positions. However, in certain applications, such as high precision liquid chromatography, interruption of the liquid flow during a hold time is a disadvantage. The performance of the liquid chromatography system is negatively affected due to the occurrence of diffusion of the components in the liquid volume held in the tubing near the dispensing means during the hold time.

It is also known to use a shunt valve to convey the liquid flow to waste during the receptacle change. This method has obviously the disadvantage that valuable substances may be present in the wasted flow, and consequently are lost.

Therefore, there is a need for a method and a device for preventing spillage when switching from one collecting receptacle to the next in a fraction collector.

SUMMARY OF THE INVENTION

In a first aspect, it is an object of the present invention to provide a method for preventing spillage when switching from one collecting receptacle to the next in a fraction collector.

This object is achieved with a method of the present invention.

According to the method of the invention, a liquid volume that should have been dispensed during a time interval necessary to switch receptacles is held in an expandable chamber. When the next receptacle is properly positioned to receive liquid, the liquid volume retained in the expandable chamber is added to the ongoing flow of liquid through the fraction collector to be dispensed into the receptacle.

In a second aspect of the present invention there is provided a device for preventing spillage when switching from one collecting receptacle to the next in a fraction collector.

In a third aspect of the present invention there is provided a fraction collector including a device for preventing spillage when switching from one collecting receptacle to the next.

In a fourth aspect of the present invention there is provided a liquid chromatography system including a device for preventing spillage when switching from one collecting receptacle to the next in a fraction collector.

Further scope of applicability of the present invention will become apparent from the detailed description given hereinafter. However, it should be understood that the detailed description and specific examples while indicating preferred embodiments of the invention are given by way of illustration only. Various changes and modifications within the spirit and scope of the invention will become apparent to those skilled in the art from the detailed description below.

Specifically, it should be noted that the use of the method and device of the invention is illustrated within the field of liquid chromatography. However, it is just as useful within any other field of application wherein there is a desire to use a fraction collector without spillage when switching from one collecting receptacle to the next.

BRIEF DESCRIPTION OF THE DRAWINGS

The present invention will become more fully understood from the detailed description given herein, including the accompanying drawings which are given by way of illustration only and thus are not limiting the present invention, and wherein.

DETAILED DESCRIPTION OF PREFERRED EMBODIMENTS

Figure 1:
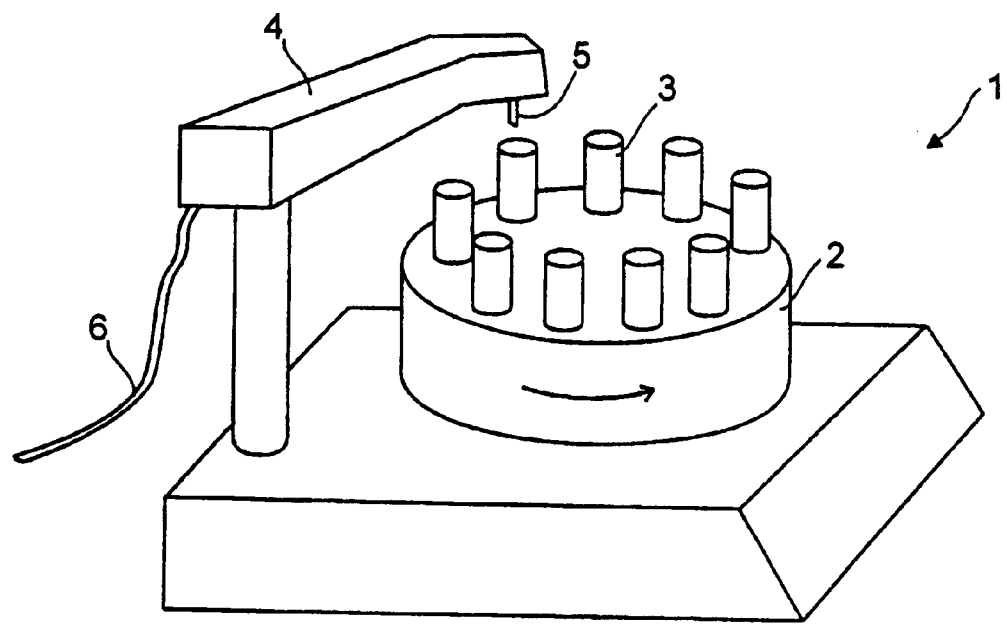
FIG. 1 is a schematical perspective view of a conventional fraction collector.

As a background, FIG. 1 illustrates schematically the basic components of a typical fraction collector 1. The collector 1 includes a tray 2 that is rotatable around its center (illustrated with an arrow). The tray 2 is provided with a rack for storing receptacles, such as tubes 3. An extension arm 4 holds a dispensing means 5, typically a syringe needle or a plastic tube. The dispensing means is in fluid communication with a feed line, consisting of an inlet tubing 6, through which liquid to be dispensed to the tubes of the fraction collector is provided from any selected equipment (not shown), such as a liquid chromatography column.

During operation, the tray 2 is rotated to place a first tube 3 below the dispensing means 5. Liquid, fed through the tubing 6 via the dispensing means 5, is discharged into the tube. When the first tube 3 has received a fraction volume of liquid, the tray 2 is rotated an angle to place a second tube 3 below the dispensing mean to receive a fraction volume. These steps are repeated a selected number of times.

It should be noted that this general description of components and operating steps of a conventional fraction collector with a rotatable tray is not intended to limit the present invention to this type of fraction collectors. It will be readily understood by anyone skilled in the art that the present invention is just as useful with any other type of conventional fraction collector. For example, a fraction collector wherein the tubes are placed below the dispensing device using linear movements, or wherein other types of receptacles than test tubes, such as microtiter plates are used could be used with the invention.

Regardless of the type of fraction collector, there is a time interval T between the moment when the first receptacle leaves the liquid flow discharged from the dispensing means and the moment when the next receptacle is in place to receive the liquid flow. Assuming that the flow rate is FR(t), wherein t indicates that the flow rate could be varying with time, a volume V is lost during the receptacle switch, provided that no measures are taken. This volume may be calculated using the formula $$V = \int_0^T FR(t) \cdot dt \qquad [1]$$

One conventional approach to avoid the spillage is to stop the flow through the dispensing means by way of a shut-off valve. Thereby no liquid is lost, but halting the flow affects the equipment upstream of the fraction collector, as well as the precision of the separation in its entirety.

Figure 2:
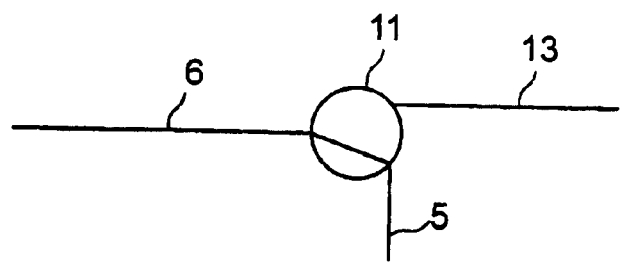
FIG. 2 is a schematical illustration of the flow paths of a conventional method for avoiding spillage during receptacle switching.

Another conventional approach, as described above and illustrated in FIG. 2, is to use a three-way valve 11 to convey the flow of liquid from the inlet tubing 6 to waste via a tubing 13 during the tube switch operation. Following the switching of tubes, the valve 11 directs the liquid into the tube via the dispensing means 5. This approach, while avoiding spillage on the fraction collector tray, will waste the volume V that could contain valuable components.

According to a first aspect of the present invention the spillage is avoided, at the same time as no liquid loss occurs, by performing the steps of
1) filling an expandable chamber with the liquid being conveyed to the dispensing means during the time interval for switching from a first to a second receptacle, and
2) emptying the liquid collected in the expandable chamber during the previous step into the second receptacle.

Figure 3A:
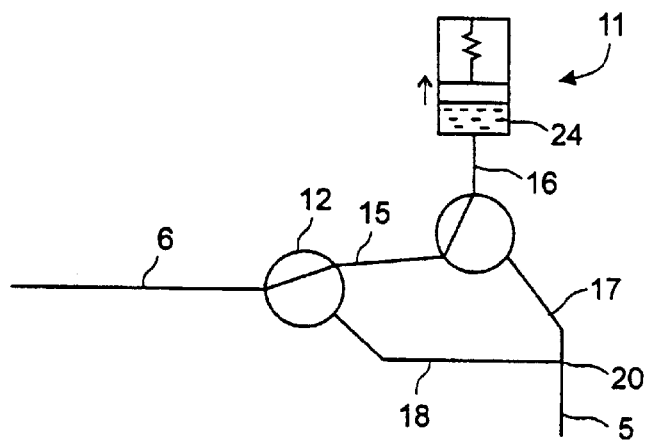
FIG. 3A is a schematical view illustrating flow paths and a device according to an embodiment of the present invention for avoiding spillage during receptacle switching, in a first operating position.
Figure 3B:
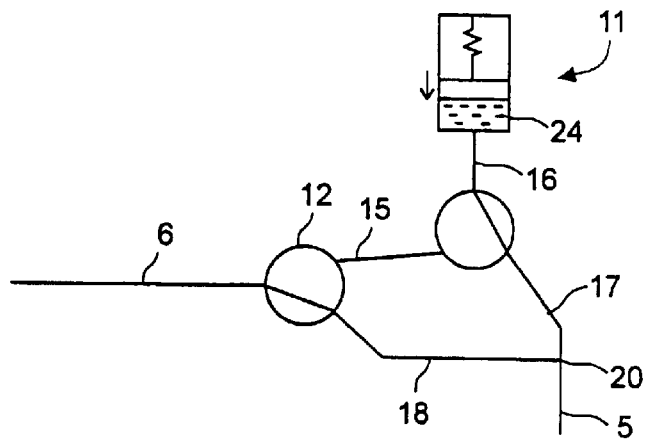
FIG. 3B is a schematical view corresponding to FIG. 3A, showing a second operating position.

An arrangement for performing the method of the invention is illustrated in FIGS. 3A and 3B. The liquid to be dispensed into the receptacles of the fraction collector is fed through the inlet tubing 6 to a first three-way valve 12. One outlet of the first three-way valve 12 is in fluid communication with a second three-way valve 13 via a tubing 15, while the second outlet of the first three-way valve 12 is in fluid communication with an inlet port of a T-connection 20 via a tubing 18. One outlet of the second three-way valve 13 is in fluid communication with a liquid holding means 16 via a tubing 16, while the second outlet of the second three-way valve 13 is in fluid communication with an inlet port of the T-connection 20 via a tubing 17. The common outlet port of the T-connection 20 is in fluid communication with the dispensing means 5.

In the first step of the method of the present invention, as shown in FIG. 3A, the first 12 and second 13 three-way valves are positioned to provide fluid communication between the inlet tubing 6 conveying liquid at a positive pressure and the liquid holding means 16 via the tubing 15. In this position, the liquid from the inlet tubing 6 is conveyed to a chamber 24 in the liquid holding means 11, which will be described in more detail below. At the same time the tubing 17 and 18, and thus the dispensing means 5, is cut from the liquid delivery from the inlet tubing 6 and consequently essentially no liquid is discharged from the dispensing means 5. The chamber 24 is expandable to receive the total volume V delivered during the receptacle-switching interval T.

In the second step, performed after the switching of receptacles, the first three-way valve 12 is positioned to convey liquid from the inlet tubing 6 to the dispensing means 5 via the tubing 18 and T-connector 20, while the second three-way valve 13 is positioned to convey liquid from the liquid holding means 13 to the dispensing means 5 via the tubing 17 and the T-connector 20.

Therefore, in the second step, a receptacle below the dispensing means 5 receives liquid delivered from the inlet tubing 6. At the same time it receives liquid, that was collected during the tube-switching time interval T, from the liquid holding means 11.

It should be noted that separate dispensing means, one from each of the three-way valves 12, 13 could be used. However, one common dispensing means is preferred since this simplifies the arrangement.

Figure 4:
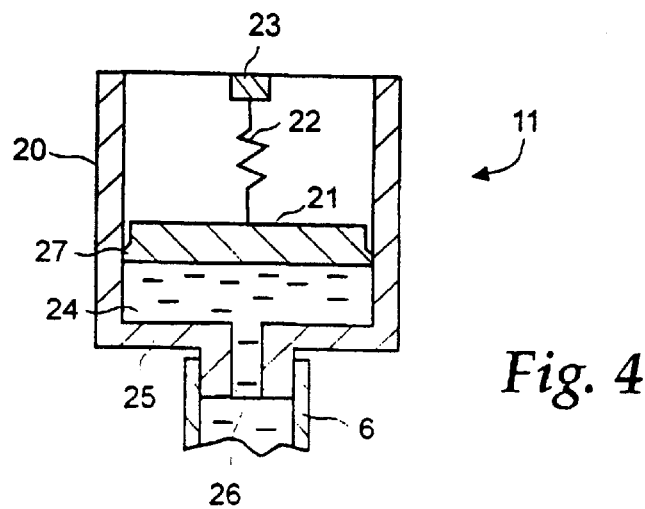
FIG. 4 is a detailed cross sectional view of a holding device according to a first embodiment of the present invention.

An embodiment of a liquid holding means 11 according to the invention, and used in the arrangement above, is shown in FIG. 4. The liquid holding means 11 includes a hollow cylindrical body 20, at one end closed by an end plate 25. An opening 26 in the end portion allow fluid communication between the tubing 16 and a chamber 24. The chamber 24 is defined by the interior wall of the cylindrical body 20, the end plate 25 and a piston member 21 being reciprocally displaceable in the axial direction of the cylindrical body. A flange 27 is provided on the cylindrical surface of the piston member 21 to seal against the cylindrical body 20 inner wall. A compression spring 22 is provided between the piston member 21 and a spring mounting means 23 attached to the upper part of the cylindrical body 20.

The spring stiffness of the compression spring 22 is selected to provide a force against the piston member being somewhat less than the pressure force built up on the wet side of the piston when the outlets to the dispensing means 5 are cut off during the first step of the method of the invention.

Thus, the pressure build-up in the liquid entering the chamber 24 forces the piston member 21 to retract in the axial direction of the cylindrical body 20, thereby enlarging the chamber 24 to hold the liquid continuously being fed via the inlet tubing 6.

During the second step of the method according to the invention, the pressure in the chamber 24 is relaxed as the outlets to the dispensing means 5 are opened. Consequently, the compressed spring 22 acts to press the piston member 21 towards the end plate 25 of the liquid holding device, thereby forcing the liquid of the chamber out through the tubing 16, via the second valve 13 through the dispensing means 5 and into a receptacle positioned below the dispensing means. At the same time liquid is dispensed into the receptacle from the inlet tubing 6 via the first valve 12.

When the chamber 24 is emptied its piston member 21 will rest until the switching to the next receptacle, and the first step of the method is repeated.

Figure 5A:
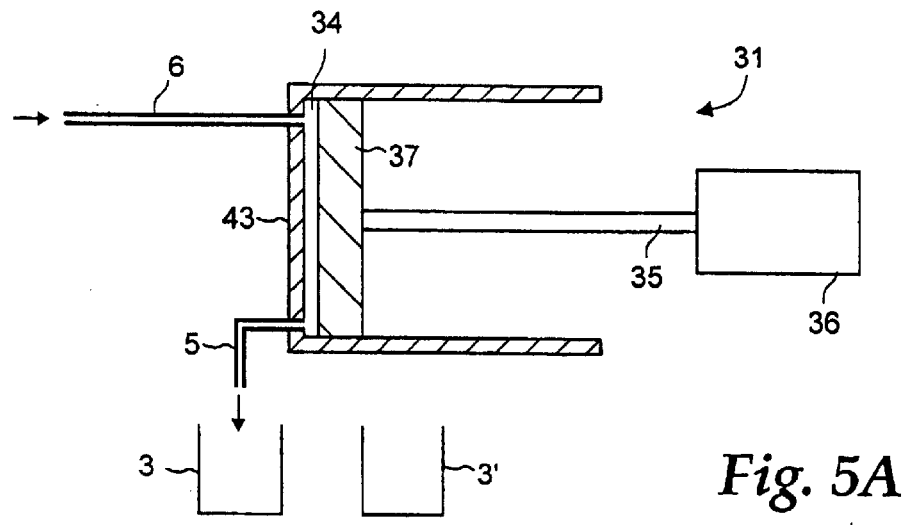
FIGS. 5A–C are schematical views illustrating flow paths and a device according to a second embodiment of the present invention, in three operating positions.
Figure 5B:
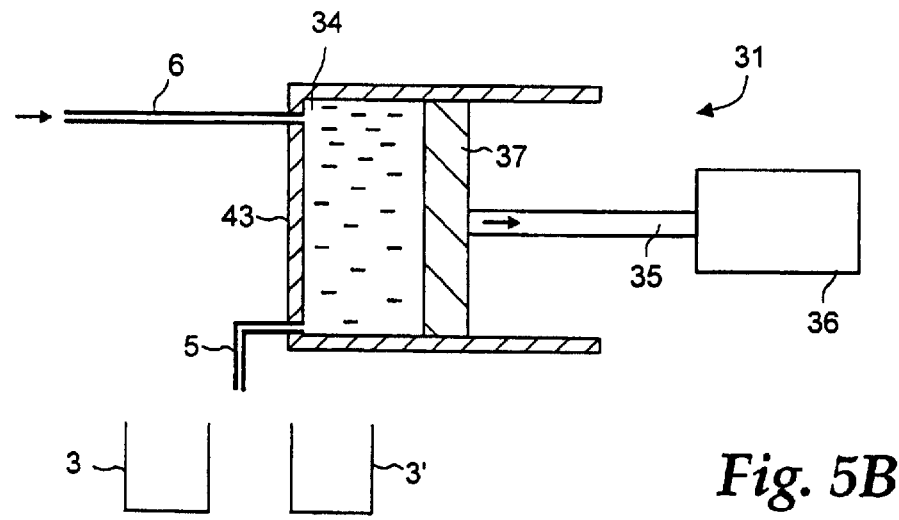
Figure 5C:
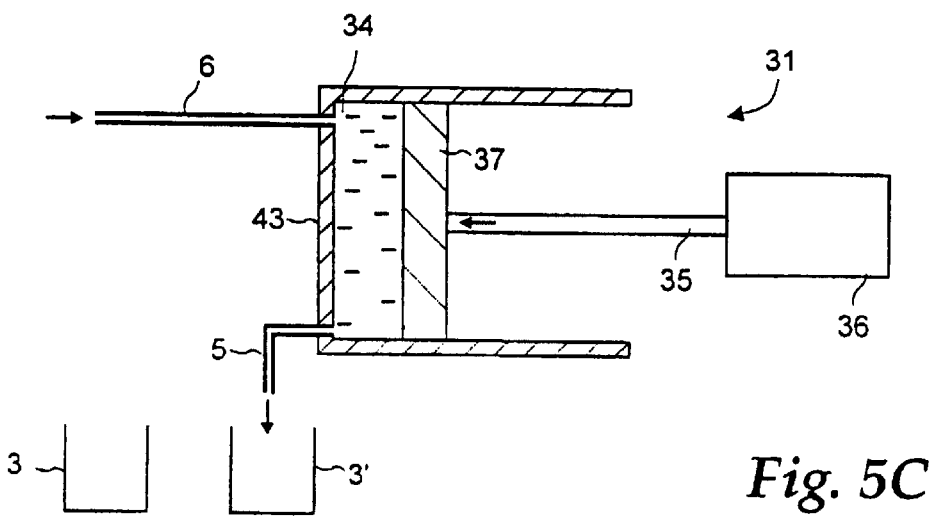

A second and preferred embodiment of a device for use with the method of the invention is illustrated in FIGS. 5A–C, 6 and 7. In FIGS. 5A–C is shown an arrangement including a second and preferred embodiment of a liquid holding means 31.

Figure 6:
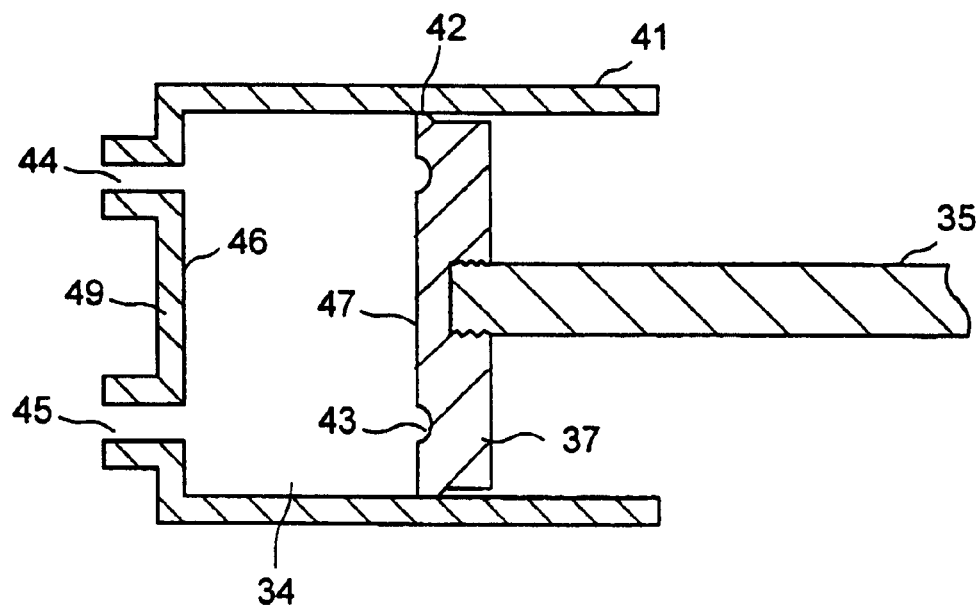
FIG. 6 is a detailed cross sectional view of a holding device according to a second embodiment of the present invention.

As shown in FIG. 6, the second embodiment of a liquid holding device is similar to the first embodiment above in that an expandable chamber 34 is defined by the inner wall of a hollow cylindrical body 41, an end plate 49 and a piston member 37.

However, the end plate 49 is provided with two openings, an inlet opening 44 and an outlet opening 45. Furthermore, a shaft 35 replaces the compression spring of the first embodiment, said shaft being controllably and reciprocally moveable in the axial direction of the cylindrical body 41. The shaft 35 and the piston member 37 are fixed to each other, for example by a threaded joint, so as to be movable as one unit.

A drive unit 36 (shown in FIGS. 5A–C), such as a linear stepping motor controlled by a microprocessor, controls the displacement of the shaft 31, and consequently of the piston member 37.

The piston member 37 is provided with a flange 42 on its cylindrical surface to seal against the inner wall of the cylindrical body 41.

Figure 7:
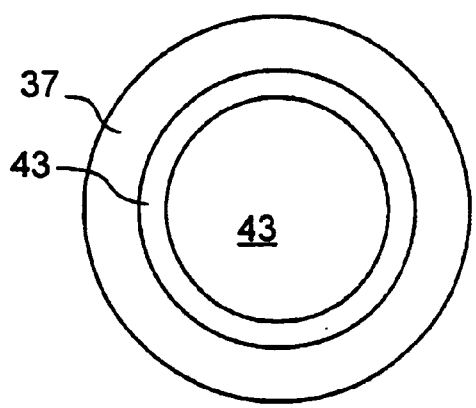
FIG. 7 is a front view of an axially moveable chamber wall.

The wet side surface 47 of the piston member 37 is provided with an annular, concentric groove 43, as shown in FIG. 6 and 7. The diameter and the width of the groove 43, as well as the width and positions of the inlet and outlet openings 44, 45 are selected to ensure that a flow of liquid entering through the inlet opening 44 in a state where the piston element 21 is in its extreme left position (when viewing FIG. 6), wherein the wet side piston surface 47 contacts the wet side surface 46 of the end plate 49, will pass to the outlet opening 45 via the groove 43.

FIG. 5A schematically illustrates a first state wherein the piston member 37 of a device according to FIG. 6 and 7 is in its extreme left position, representing the case wherein liquid being fed via the input tubing 6 is discharged to a receptacle 3 via the groove 43 and the dispensing means 5.

FIG. 5B schematically illustrates a second state occurring during the time interval T for switching from on receptacle 3 to the next receptacle 3'. In this second state, the piston member 37 is pulled backwards by the drive unit 36 acting on the piston shaft 35. The liquid coming from the input tubing 6 is thereby sucked into the expanding chamber 34 of the liquid holding means 31, while no liquid is discharged through the dispensing means 5.

FIG. 5C schematically illustrates a third state occurring after the moment when the next receptacle 3' is situated below the dispensing means 5. In this third state, the piston member 37 is pushed forward by the drive unit 36 acting on the piston shaft 35. The liquid previously hold in the chamber 34 is pressed out through the outlet opening 45 to the next receptacle 3' via the dispensing means 5. Simultaneously, liquid being fed via coming from the input tubing 6 is also discharged to the next receptacle 3' via the chamber 34 and the dispensing means 5. This third state is present until the piston element is returned to its extreme left position, wherein the first state according to FIG. 5A occurs.

This second embodiment is preferred since it minimizes the dead volume in the flow path between the inlet tubing 6 and the dispensing means 5, said dead volume actually being close to zero.

When designing a liquid holding device according to the present invention, measures and materials for the different components of the device have to be selected based on the requirements put by the application at hand, as is natural for anyone led in the art. However, certain principles have to be taken into consideration when designing a device according to the second embodiment of the present invention.

Thus, the piston member 37 should be pulled out at a rate correlated to the flow rate in the inlet tubing 6, i.e. the liquid volume being fed through the inlet tubing per time unit (as calculated with a formula such as the eq. [I] above) always is substantially equal to, or possibly somewhat less than, the volume created in the expanding chamber 34. Otherwise, liquid will flow to the dispensing means.

Furthermore, the piston member 37 should be pushed forward at a rate correlated to the pressure in the inlet tubing 6, as well as to the flow-through capacity of the outlet opening 45, such that the flow from the inlet tubing will pass through the chamber 34 virtually undisturbed at the same time as the liquid volume previously held in the chamber is discharged to the dispensing means. Otherwise, the resolution of separated substances within the liquid could be negatively affected.

Although not shown, as for the first embodiment it would be possible to use two dispensing means, i.e. an additional separate dispensing means for dispensing the liquid of the holding device into the receiving receptacle. However, this is assessed to be unnecessarily complicated for most applications.

In addition to a device according to the invention, a system utilizing the method of the invention, such as a liquid chromatography system including a fraction collector, should also include control means for correlating the operation of the liquid holding means and the fraction collector. This control means could be established by any suitable means, such as a personal computer together with suitable interface circuits commonly known within the art.

Figure 8:
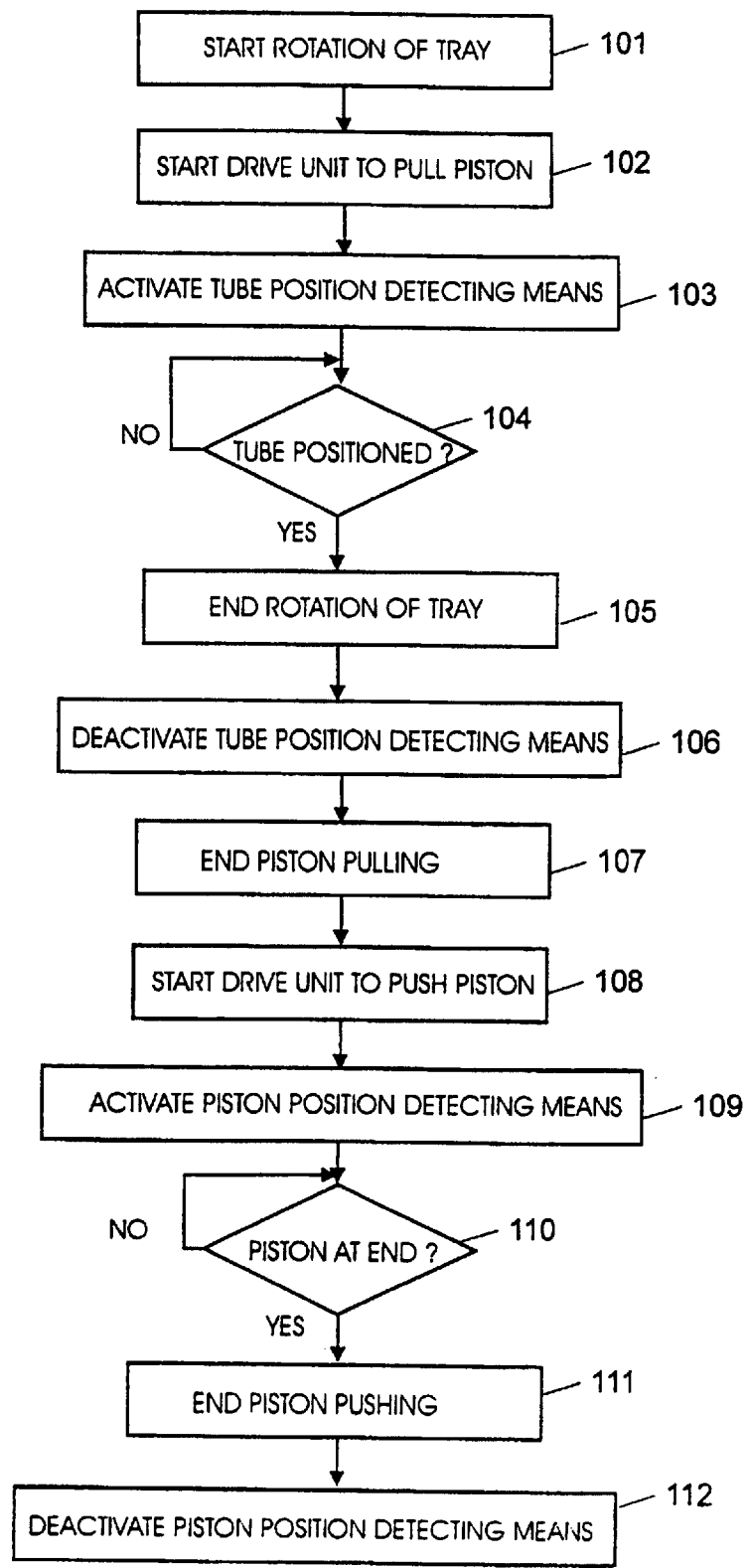
FIG. 8 is a flow chart showing the operation of a control means for controlling a fraction collector and liquid holding means according to the present invention.

A flow chart, showing control steps to be executed by such a control means is shown in FIG. 8 for the case of a fraction collector with a rotatable tray holding test tubes in a circular pattern around the rotational axis of the tray and being equipped with a liquid holding device according to the second embodiment described above. Of course, anyone skilled in the art could convert the commands of the flow chart to any other type of fraction collector or to the steps necessary to control the valves of the first embodiment of liquid holding device as described above.

Depending on the application, different types of criteria for initiating the switching of receptacles could be used such as detecting a liquid level in a receptacle, calculate a delivered liquid volume, monitoring a property significant for substances transported in the liquid etc.

Regardless of the criteria selected, the control means begins the receptacle switching by starting the rotation of the tray 101, activating the drive unit 36 to pull the piston element 37, thereby sucking liquid into the expanding chamber 34, and activating a tube position detecting means 103. Tube position detecting means (not shown) could be any conventional device used for the purpose, such as a photocell.

The control means awaits a signal 104 from the tube position detecting means to indicate that the next tube is in a proper position to receive liquid. When this signal is received, the control means ends the tray rotation 105, deactivates the tube position detecting means 106, and stops 107 the drive unit 36 from pulling the piston element. At that moment, liquid from the inlet tubing 6 flows towards the dispensing means 5 via the outlet opening 45.

Next, the control means commands the drive unit to push the piston 108 to compress the chamber, thereby discharging the content of the chamber through the outlet opening 45. Furthermore, the control means activates a piston end position detecting means (not shown) 109, operative to indicate when the piston reaches its bottom position, i.e. when the chamber 34 has its minimum volume.

The control means monitors the piston end position detecting means 110, until it detects a signal indicating that that the piston has reached is bottom position and, consequently, the previously collected liquid has been discharged. At this moment, the control means stops the drive unit pushing the piston 111, and deactivates the piston end position detecting means 112.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Of course, it should also be realized that although liquid chromatography has been used as a suitable example of a field of application, the application of the method and the device of the invention is not restricted to this field.

What is claimed is:

1. In a method for avoiding loss of liquid during fraction collecting when switching dispensing from a first receptacle (3) to a second receptacle (3'), for use with a fraction collector (1) which receives liquid via a feed line (6) to discharge the liquid through a dispensing means (5) to receptacles (3, 3'), and which switches a first receptacle (3) to a second receptacle (3') at a selected point in time, the improvement comprising the steps of:

providing said fraction collector (1) with a device for temporarily holding liquid to be discharged to a receptacle (3'), said device including an inlet (15, 44) for receiving liquid from said feed line (6), and an outlet (17, 45) for discharging the liquid received via the inlet (15, 44), and an expandable chamber (24; 34) in the flow path between the inlet (15, 44) and the outlet (17, 45), filling (102) said expandable chamber (24; 34) with liquid being conveyed towards the dispensing means (5) during the time interval of switching from the first receptacle (3) to the second receptacle (3'); and emptying (108) the liquid collected in the expandable chamber (24; 34) into the second receptacle (3').

2. A fraction collector (1) which receives liquid via a feed line (6) to discharge the liquid through a dispensing means (5) to receptacles (3, 3'), and which switches from a first receptacle (3) to a second receptacle (3') at a selected point in time, comprising a device for temporarily holding liquid to be discharged to a receptacle (3') during the time interval of switching from the first receptacle (3) to the second receptacle (3'), said device including an inlet (15, 44) for receiving liquid from said feed line (6), and an outlet (17, 45) for discharging the liquid received via the inlet (15, 44), and an expandable chamber (24; 34) in the flow path between the inlet (15, 44) and the outlet (17, 45).

3. The fraction collector of claim 2, wherein said expandable chamber (24; 34) is defined by at least one movable wall (21; 37) being displaced in response to the liquid volume being entered into said chamber (24; 34).

4. The fraction collector (1) of claim 3, wherein said movable wall (21; 37) is coupled to a drive unit (36) for displacing said wall in response to the liquid volume being entered into said chamber (24; 34).

5. A device for temporarily holding liquid to be discharged to a receptacle (3'), said device being in fluid communication with the flow path through the fraction collector of claim 2, said device including an inlet (15, 44) for receiving liquid from a feed line (6), and an outlet (17, 45) for discharging the liquid received via the inlet (15, 44), and comprising an expandable chamber (24; 34) in the flow path between the inlet (15, 44) and the outlet (17, 45).

6. A liquid chromatography system, including a fraction collector (1) for dispensing a liquid into receptacles (3, 3'), and which switches dispensing from a first receptacle (3) to a second receptacle (3') at a selected point in time, comprising a device for temporarily holding liquid to be discharged to one of the receptacles (3') during the time of interval of switching from the first receptacle (3) to the second receptacle (3'), said device being disposed in fluid communication with the flow path through the fraction collector, said device including an inlet (15, 44) for receiving liquid from a feed line (6), and an outlet (17, 45) for discharging the liquid received via the inlet (15, 44), and comprising an expandable chamber (24; 34) in the flow patch between the inlet (15, 44) and the outlet (17, 45).

* * * * *